United States Patent
Du et al.

(10) Patent No.: US 10,531,809 B2
(45) Date of Patent: Jan. 14, 2020

(54) WEARABLE HEARTBEAT AND BREATHING WAVEFORM CONTINUOUS MONITORING SYSTEM

(71) Applicants: Xiaosong Du, San Ramon, CA (US); Yuxin Zhou, Fremont, CA (US)

(72) Inventors: Xiaosong Du, San Ramon, CA (US); Yuxin Zhou, Fremont, CA (US)

(73) Assignee: Bayland Scientific LLC, San Ramon, CA (US)

( * ) Notice: Subject to any disclaimer, the term of this patent is extended or adjusted under 35 U.S.C. 154(b) by 0 days.

(21) Appl. No.: 14/284,655

(22) Filed: May 22, 2014

(65) Prior Publication Data

US 2014/0350424 A1     Nov. 27, 2014

Related U.S. Application Data

(60) Provisional application No. 61/826,025, filed on May 22, 2013.

(51) Int. Cl.
*A61B 5/0452* (2006.01)
*A61B 5/0432* (2006.01)

(52) U.S. Cl.
CPC ........ *A61B 5/04525* (2013.01); *A61B 5/0432* (2013.01)

(58) Field of Classification Search
CPC ............ A61B 5/04525; A61B 5/02438; A61B 5/14551; A61B 5/7264; A61B 7/003; A61B 2560/0412; A61B 5/113; A61B 2562/0219; A61B 5/02444; A61B 5/0432; A61B 5/6898
USPC ....................................................... 600/523
See application file for complete search history.

(56) References Cited

U.S. PATENT DOCUMENTS

| 8,323,188 B2 | 12/2012 | Tran ............................. 600/300 |
| 8,328,420 B2 | 12/2012 | Abreu .......................... 374/208 |
| 2007/0049837 A1* | 3/2007 | Shertukde ............ A61B 5/0408 600/528 |

(Continued)

OTHER PUBLICATIONS

Trayanova: Computational Cardiology: The Heart of the Matter, ISRN Cardiology, vol. 2012, article ID 269680, accepted Sep. 6, 2012.*

*Primary Examiner* — Carl H Layno
*Assistant Examiner* — Erin M Piateski
(74) *Attorney, Agent, or Firm* — Helen Mao; Imperium Patent Works

(57) ABSTRACT

Apparatus and method are provided to collect and analyze heartbeat waveforms. In one novel aspect, the heartbeat waveforms are collected from wearable devices. In one embodiment, the wearable device collects heartbeat waveforms by attaching the device to the patient for a long period and sends the collected waveforms to a receiver through a wireless network. In another novel aspect, an application program is installed in a smart device to receive heartbeat waveforms from one or more wearable devices. The application program either relays the received waveform to a remote processing center or processes the data before sending. In another novel aspect, an analysis method compares received patient's current heartbeat waveform with historic data. In one embodiment, the historic data are stored in a cloud-based database. In another novel aspect, the remote processing center is an open platform data center, which takes in certified third party inputs.

14 Claims, 9 Drawing Sheets

(56) References Cited

U.S. PATENT DOCUMENTS

| | | | |
|---|---|---|---|
| 2008/0103405 A1* | 5/2008 | Banet | A61B 5/0002 600/523 |
| 2009/0105605 A1* | 4/2009 | Abreu | A61B 5/0008 600/549 |
| 2011/0184297 A1* | 7/2011 | Vitali | A61B 5/04017 600/509 |
| 2011/0224565 A1* | 9/2011 | Ong | G06F 19/345 600/509 |
| 2012/0095352 A1* | 4/2012 | Tran | A61B 5/0022 600/490 |
| 2012/0215123 A1* | 8/2012 | Kumar | A61B 5/0006 600/523 |
| 2012/0220835 A1* | 8/2012 | Chung | A61B 5/0022 600/301 |
| 2013/0060480 A1* | 3/2013 | Korhonen | A61B 5/1118 702/19 |

* cited by examiner

WEARABLE HEARTBEAT AND BREATHING WAVEFORM CONTINUOUS MONITORING SYSTEM

CROSS REFERENCE TO RELATED APPLICATIONS

This application claims priority under 35 U.S.C. § 119 from U.S. Provisional Application No. 61/826,025 entitled "METHOD AND APPARATUS OF COMPACT WEARABLE HEART BEAT WAVEFORM AND BREATH WAVEFORM CONTINUOUS MONITORING SYSTEM," filed on May 22, 2013, the subject matter of which is incorporated herein by reference.

TECHNICAL FIELD

The present invention relates generally to mobile heartbeat and breathing waveform continuous monitoring and, more particularly, devices and system for an open platform continuously monitoring heartbeat and breathing waveform obtained from remote wearable devices.

BACKGROUND

For the past decade, there are significant progresses in medical research. The Human Genome Project had finished. For the first time in history, we have decoded over 20,000 human genes. The stem cell researchers have already safely injected stem cells into patients with neurodegenerative diseases and spinal cord injuries and they've seen the potential to vastly improve lives. MRI and other medical imaging technologies continuously improved, more and more advanced electronic devices, sensors, networking, data mining technologies are used in hospitals. Despite these great achievements, most of us still rely on once or twice annual doctor visits to get our physicals. None of these great technologies is used to monitor our day-to-day health status, not mention more sophisticated day to day health analysis and disease detection. Many people jokes that they know their cars better than their bodies. In many ways, it is a true statement. There are over 100 sensors on a modern car. On the other hand, the sensor to monitor our vital life is close to zero.

Meanwhile the rapid advancement of mobile Internet and smart phone has changed our daily life, and changed how the world operates in many ways. It also drives the semiconductor industry and related other industries to make the microcontrollers, various sensors and wireless communication chips very small with very low power consumption. Meanwhile, the prices of these devices drop dramatically in the past few years, which make them affordable to general public. However, how to take advantage of these latest technologies for medical use remains a challenge.

In the past, many body vital sensors have been developed. For example, in U.S. Pat. No. 8,328,420, Abreu et al. disclosed how to measure brain temperature by wearing a special glass that embedded with sensors. But most of these sensors are designed to be used in a clinic environment. The size is large and cumbersome. In many cases, professional help is needed to put on these sensors, and large instruments are needed to collect the outputs. Recently, efforts have been made to use microcontroller with analog to digital convertors to digitize the traditional analog sensor outputs and transmit the results through wired or wireless network to a data-collecting center. For example, in U.S. Pat. No. 8,323,188, Tran disclosed how to digitize the sensors input and transmit the result to remote server so that medical professionals, user's relatives can monitor the health condition of the user. After the booming of smart phone, new effort has been made to develop digital-watch kind of device, which can sense user's pulse, blood pressure, and other vital health data, and send these data through wireless network to a data-collecting center.

However, there are several drawbacks of the prior arts. Many of these sensors, like ECG, need to put multiple probes on different parts of the body. Some of them, like the ultrasonography, need to apply special gels on the body. In the clinic environment, with medical professional's guidance, they are fine. But for normal user's day-to-day use, it becomes inconvenient and sometime even not applicable. The next issue is how to amount the sensors on the human body so that the user can do long term monitoring without discomfort. It is preferable that the user can still conduct normal daily business during the monitoring. For general public day-to-day use, the sensors are not only affordable, but also cheap enough that the user can replace them in a short period. There are more challenges at the server side. Most of the prior arts and applications only use the server to collect data, and let the medical professionals to analyze the results and draw conclusions. This procedure can only be applied to the general clinic application with only hands full of patients. When there are millions of users start to upload their daily vital health data to the server, the process has to be automated.

SUMMARY

Apparatus and method are provided to monitor heartbeat waveform and breathing waveform continuously.

In one novel aspect, a wearable waveform-collecting device can be attached to a human body to collect heartbeat and/or breathing waveforms continuously. The wearable waveform-collecting device transmits the collected information to a smart device.

In one embodiment of the present invention, a digital movement sensor is used to detect chest skin's movement. The digital movement sensor can be a gyroscope, or an accelerometer.

In another embodiment of the present invention a digital acoustic sensor is used to collect acoustic signals from the user. The digital acoustic sensor can be a microphone, a piezo sensor, or any other sound detector with an analog-to-digital converter.

In yet another embodiment of the present invention, a series of acoustic sensors are designed to receive sound from different direction to enhance to noise immunity.

In another embodiment of the present invention, a miniature stethoscope head can be employed to enhance the acoustic signal from the body. In the scenario of using a series of acoustic sensors, multiple miniature stethoscope heads can be employed.

In yet another embodiment of the present invention, an adjustable gain setting is provided in analog or digital means to provide the capability of trade-off the range and sensitivity according to different skin condition of different people.

In yet another embodiment of the present invention, an algorithm to use the movement sensor data together with the acoustic sensor to enhance the system's noise immunity and provide other body environment information such as walking pace, loud background, and loose contact induced false data.

In another embodiment of the present invention, two different wavelength LEDs are used as the light sources for detecting blood oxygen level. The LEDs can be turned on and off through wired or wireless network using smart phone, computers and other smart devices.

In yet another embodiment of the present invention, a compact battery is used to allow long operation span with light weight.

In yet another embodiment of the present invention, a wireless communication module is included to transfer data to remote processor to use its computing power. In addition, a read-out I/O, such as SD card, or micro SD card, is used to store the waveform locally if the remote host is not available.

In yet another embodiment of the present invention, the waveform collecting and transmission module can be associated with a smart portable device, such as smart phone, tablet, etc. It can be an auxiliary component that mounts on the case, and the smart device can be used to charge the battery of the waveform collecting and transmission module.

In yet another embodiment of the present invention, a silicone sheet, like "ScarAway", can be used to mount the waveform collecting and transmission module onto the body. For matured female, a special designed bra can be used to mount the device. For athletes and other users with very active movements, an elastic belt can be used to mount the device.

In another novel aspect, a heartbeat application program in a smart device enables the smart device to receive waveform information from one or more wave collecting-devices. The heartbeat application sends heartbeat information to a service platform via network connections.

In one embodiment of the present invention, a smart phone, tablet, or other smart device is used to set up, to control and to charge the waveform collecting and transmission module. It is also used to collect the waveform data through wireless network; then transmit the waveform data to remote data centers through wireless network for further analysis and archive. The user can use the screen of the smart device to view the waveform to make sure the waveform collecting and transmission module is mounted correctly. The user can use the screen to view the analysis and characterization results, get advices and alarms from the remote data center. The user can put finger between the camera or photodiode of the smart device and the LEDs on the waveform collecting and transmission module. The camera or photodiode of the smart device can be used to capture the light from the LEDs which penetrates the user's finger. The captured images or light strengths can be used to calculate the blood oxygen level of the user.

In yet another embodiment of the present invention, a notebook, desktop computer or dedicated local server can be used to collect the waveform data from the waveform collecting and transmission module. It can be used to set up, control and charge the waveform collecting and transmission module. The collected waveform data can be stored, archived locally, and can be uploaded to remote data centers through wired or wireless network. The user can use the screen of the notebook, the desktop computer or the local server to view the analysis and characterization results, get advices and alarms from the remote data centers.

In another novel aspect, a data processing center retrieves archived historic waveform information of a patient and compares with the current waveform information of the same patient. The data processing center generates a report using predefined algorithms based on the current waveform information and the retrieved historic waveform information.

In one embodiment of the present invention, data centers are used to collect the waveform, store and archive the waveform. Various data processing algorithms are applied to the collected waveform to characterize the waveform. The data centers consist of frontend web servers, backend databases, data processing servers and high speed network to connect them together.

In another embodiment of the present invention, environment noise is filtered out from the collected waveform. Certain sections of the collected waveform can contain signals that are not valid human body signals, for example, the environment signals, very weak signals due to the improper mounting of the collecting device, etc. Invalid sections of waveform are identified and stripped out from further analysis and characterization. For the valid waveform, data analysis algorithms are applied to extract characterization parameters. These parameters are used to compare against user's historic parameters, against his or her peer parameters and against various known disease parameters. Abnormal sections can be identified and recorded. The original waveform, the analysis and characterization results are stored and archived into the database. Based on analysis and characterization results, alarms or recommendations can be given to the user through email, SMS, web or other communication channels per user's preference. The user can always login to the website to browse through the current waveform, analysis and characterization results, and historic records.

In yet another embodiment of the present invention, based on user's CT, MRI image, blood tests, blood pressure, and other measurements, a computational cardiology model can be built and stored at the data centers. The data center servers can use this model to predict the user's heart waveform. This waveform can be used to compare with the waveform collected from the user. The servers will adjust the model's parameters so that the computed waveform will match the collected waveform. The servers will inform the user about adjustment, and tell the user if the adjustment is towards more health direction or another way around. After several rounds of adjustments, if the server still cannot successfully predict the waveform, the server will recommend the user to do another round of examinations so that the new examination results can be used to re-calibrate the model.

In another novel aspect, an open platform is used to process the data.

In one embodiment of the present invention, the user can manage his or her data privacy through the web site. The user can give permission to his or her doctors so that the doctors can use the waveform and analysis and characterization results as reference for further diagnoses. The user can determine if the data can be released to medical research institutes or professionals for research use.

In another embodiment of the present invention, after certification process, the medical researchers, data process and data mining expertise with proper credential can utilize the waveforms with users' permission to develop various algorithms to diagnose diseases, give early alarms, do data mining to explore under what kind of life-styles or genetic patterns can lead to diseases.

BRIEF DESCRIPTION OF THE DRAWINGS

The accompanying drawings, where like numerals indicate like components, illustrate embodiments of the invention.

DETAILED DESCRIPTION

Reference will now be made in detail to some embodiments of the invention, examples of which are illustrated in the accompanying drawings.

Based on technologies achievements and their broad acceptance, it is feasible to develop a set of sensors to monitor our daily vital health status, transfer these data through wired or wireless Internet to the Cloud storage. These data are archived and analyzed against the user's previous data and against various disease patterns. Health advices can be given as the result of the analysis. Furthermore, the archived data can be used by medical professionals to diagnose diseases. Sophisticated data mining can be performed on the vast daily health data from millions of people. It is very likely to lead to new medical discoveries.

The present invention provides a method, an apparatus, a computer program and a system that provides a series of compact digital sensors that is wearable by patching. The measured waveform is transferred to remote processor in real time or off-line by wireless link or readout I/O devices. The continuously monitoring waveform for a long time span, more than several hours, helps to disclose any early abnormalities. The continuously monitored waveform is characterized and compared with a database of large size samples, which include the user's previous waveforms and characterizations and various known disease waveforms and their characterizations. The user can browse the current and historic waveforms and characterizations through smart phones, smart watch, computers and other browsing devices. The health alarms or recommendations to the user can be drawn from the characterizations. The user can use them as reference and pursue further medical help. The waveforms and characterizations are automatically archived. With the user's permission, these waveforms and characterizations can be released to medical professionals or other institutes for further analysis or reference. The medical researchers, data processing and data mining expertise can utilize the large amount of waveforms and characterizations to do in depth research and exploration. Their research can lead to more advanced method for waveform analysis and characterization, which can apply to the general users. The users can choose what kind of advanced analysis they want to apply. Certain charges can be associated with the advanced analysis so that the researchers and expertise can be awarded by their discoveries.

Figure 1:
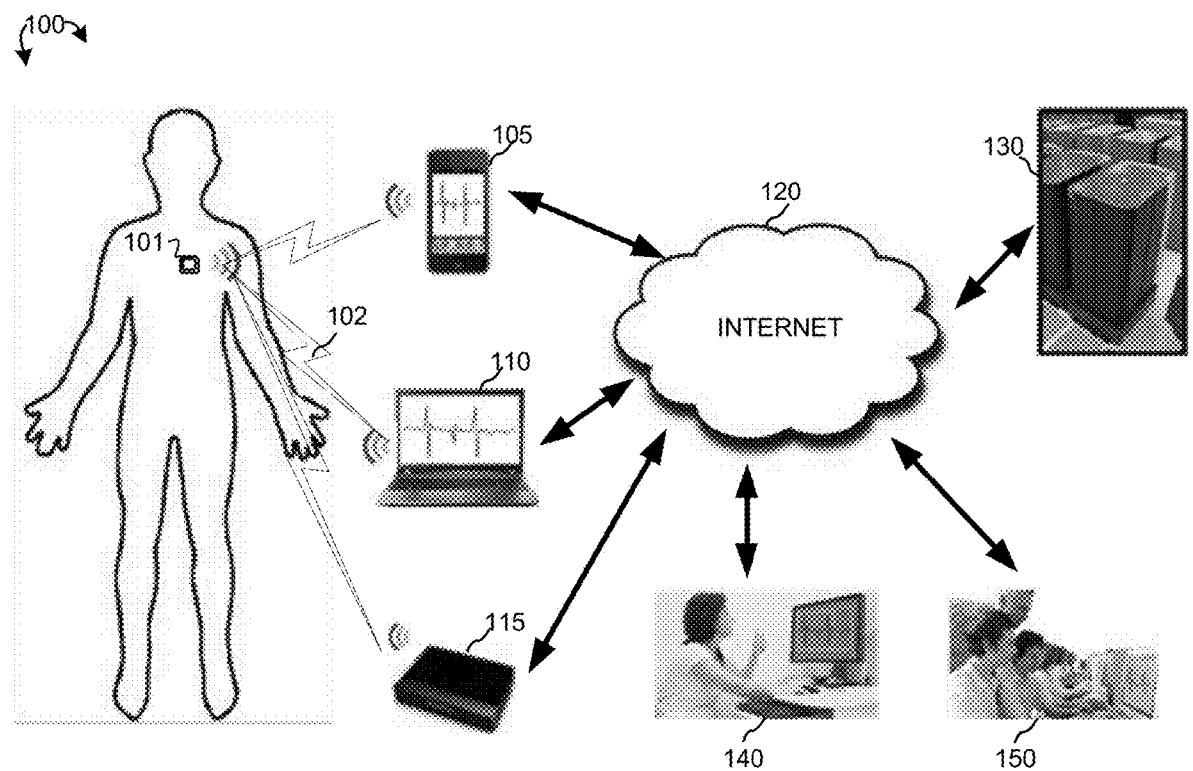
FIG. 1 is a schematic view of a continuous heartbeat and breathing waveform monitoring system in accordance to embodiments of the current invention.

FIG. 1 is a schematic view of a continuous heartbeat and breathing waveform monitoring system 100 in accordance to embodiments of the current invention. System 100 consists of a waveform collecting and transmission module 101, a local wireless network 102, smart terminals and local storage 105, 110, 115, an Internet 120, remote data centers 130, terminals for medical institute and professional 140, and third party data mining and analysis group 150.

Waveform collecting and transmission module 101, also referred as front end module, patches on the chest of the user using silicone gel kind of patch, such as "ScarAway", or other similar patches. It uses acoustic-to-electric sensors such as microphone or piezo sensors behind the shell to detect the acoustic signal. It uses a digital movement sensor, such as gyroscope or accelerometer, to detect skin's movement, which reflects the breath. Analog-to-digital convertors are employed to transfer the waveforms into digital format. The digitized waveforms can be stored into the module's local storage, such as miro-SD card. Waveform collecting and transmission module 101 can store the measured waveforms for a period. In one embodiment, upon detecting available local wireless access, waveform collecting and transmission module 101 automatically upload the stored waveforms. In another embodiment, Waveform collecting and transmission module 101 may periodically looking for wireless access to upload the stored waveforms. In yet another embodiment, the measured waveform may be uploaded directly without storing. Waveform collecting and transmission module 101 can communicate with smart device 105, such as smart phone, tablet, smart watch or other devices, through local wireless network 102, such as Bluetooth or Wifi. It can communicate with laptop or desktop computer 110 through wireless network 102 or wired connection such as USB. It can also communicate with a dedicated local server 115 through wireless network or wired connection. The smart device, computer or local server can be used to set up and control the module, monitor the waveform in real time, browse the stored waveforms, transfer the stored the waveforms to their local storages, and relay the transmission through a wired or wireless networks 120 to a remote data centers 130. The smart device, computer or the local server can be used to receive the analysis report, alarm, and advices from the remote data centers for user to review.

Remote data centers 130 collect waveforms from many waveform collecting and transmission modules. These waveforms are archived and stored in remote data centers 130. Remote data centers 130 automatically analyze and characterize the collected waveforms. Remote data centers 130 compare characterization results the corresponding patient's short term historic waveform which collected within a quarter and long term historic waveforms which collected from half year ago, a year ago and so on. Remote data centers 130 also store one or more disease patterns. These disease patterns can be preconfigured or dynamically updated. Remote data center 130 compares each corresponding patient's results various disease patterns. Remote data center 130 can choose one more disease patterns for comparison based on system input or user instructions.

A computational cardiology model can be employed to predict the user's waveform. The difference between the real waveform and predicted waveform are examined automatically by remote data centers 130 so that the model can be adjusted to match the real waveform. Remote data centers 130 adjusts the cardiology model either towards healthy direction or unhealthy direction based on predefined algorithms. The predefined algorithms can be preconfigured or dynamically updated. Reports are automatically generated and sent to an authorized user. The authorized user, such as the patient or physicians, can also login the website of remote data centers 130 to view the report and historic data.

In one embodiment of the current invention, with the authorized user's permission, the waveforms and analysis results can be retrieved and reviewed by medical institute or professionals 140. Medical institute or professionals 140 can use the retrieved information for disease diagnosis or medical research usage. The medial researchers, data processing expertise from third party with permission can utilize the waveforms granted by the users to do further analysis. In one embodiment, remote data centers 130 uses the research results as third party analysis methods. The user can subscribe certain third party analysis methods. Certain charges can be applied to the user for using the third party analysis methods. System 100 can also be used to monitor other body waveforms in similar manners. For example, similar system can be used to monitor the baby heartbeat for pregnant women. In such system, a Waveform collecting and transmission module can be attached to the abdominal area of the pregnant woman and collects baby's heartbeat for further process and analysis.

Figure 2:
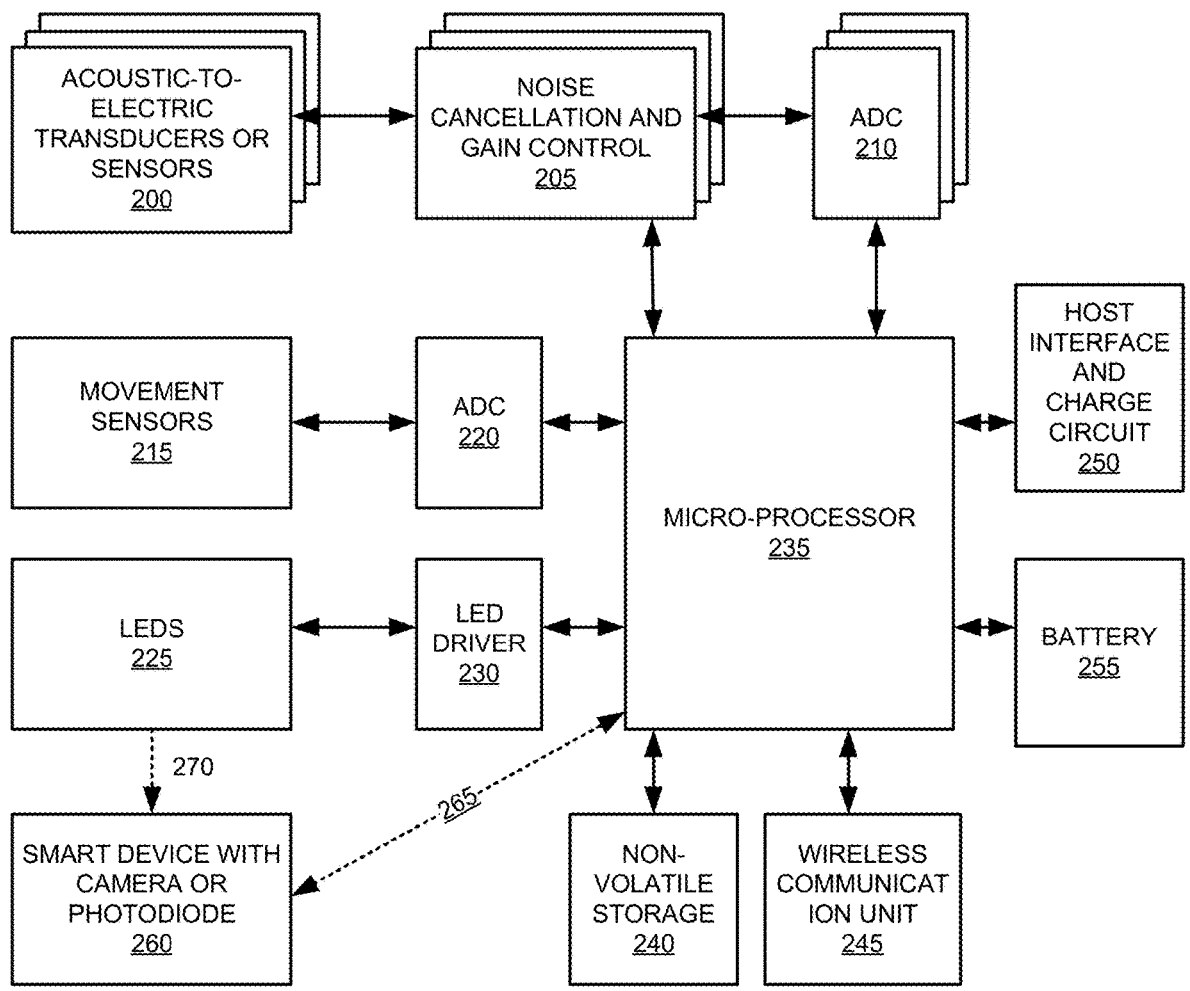
FIG. 2 is an exemplary circuit block diagram of a waveform collecting and transmission module in accordance to embodiments of the current invention.

FIG. 2 is an exemplary circuit block diagram of a waveform collecting and transmission module in accordance to embodiments of the current invention. The electronic circuit of the waveform collecting and transmission module has a battery unit 255, which provides sufficient power to last overnight measurement. Battery unit 255 supplies power to all the functional blocks in FIG. 2. A micro-processor 235 is employed to monitor the voltage level of the battery, calculate the battery's energy status and avoid system brown out. An acoustic-to-electric sensors 200 collects acoustic signals and converts it to electric signals. Acoustic-to-electric 200 can be a simple microphone or a few microphones or piezo sensors to make up an array to have better noise immunity by obtaining better background measurement and better directive measurement. The sound from the body is measured by the sensor and the output of the sensor is electrical signal. The output electrical signal is connected to a noise cancellation and gain control circuit 205, which is employed to cancel out environment noise, and enhance the body signal level. Micro-processor 235 is used to control this circuit. After noise cancellation and signal enhancement, the electric signal is connected to analog to digital converter (ADC) 210 to digitize. The result is sent to microprocessor 235. A movement sensor 215 measures the body moment. Movement sensor 215 can be a gyroscope or an accelerometer. It measures the movement of the skin on the chest caused by the heartbeat. Movement sensor 215 measures the movement and outputs electrical signal, which is connected to ADC 220. The digitized result from ADC 210 is collected by micro-processor 235. The data collected from movement sensor 215 can also tell the subject's other movement such as walk, jog, and other posture movements to help data analysis.

LEDs 225 with different wavelengths in conjunction with smart device camera or photodiode are used to measure the blood oxygen level. In one embodiment, two LEDs are used. Micro-processor 235 controls LED driver circuits 230 to turn on/off the LEDs. In one embodiment, micro-processor 235 controls LED driver circuits 230 through its I/O pins. A user can use a smart device with camera or photodiode 260 to send commands to microprocessor 235 through wireless connection 265 to turn on/off the LEDs. For example, during a blood oxygen level measurement, smart device 260 can send predefined control signals to micro-processor 235 through wireless connection 265. Mirco-processor 235 upon receiving the control signal from smart device 260, controls LEDs 225 to turn on or off. The camera or photodiode on the smart device 260 can be used to detect the lights from the LEDs. Device 260 is calibrated with the strength of received LED light. In one embodiment, smart device 260 measures the oxygen level of the blood by detecting the light strength emitted from LEDs 225 based on proper calibration. Meanwhile, LEDs 225 with visible wavelength can be used as status indicator.

Micro-processor 235 connects to non-volatile storage 240, such micro-SD. The digitized waveforms can be stored into the non-volatile storage with time stamp so it can be retrieved by smart device 105, computer 110 or local server 115, and further sent to remote data centers 130. Microprocessor 235 connects to a wireless communication module 245 so that it can communicate with smart device 105, computer 110 or local server 115 through local wireless network, such as Bluetooth, Wifi, et al. Microprocessor 235 also connects to a host interface module with battery charge circuit 250 so that it can communicate with host device, such as smart device 105, computer 110 or local server 115 through wired cable, for example USB. It also uses this cable to charge the internal battery 255.

In one embodiment, micro-processor 235 processes the measured data and analyzes them. For example, an algorithm can be employed by the microprocessor 235 to use the movement sensor data together with the acoustic sensor to enhance the system's noise immunity and provide other body environment information such as walking pace, loud background, and loose contact, which induces false data.

Figure 3:
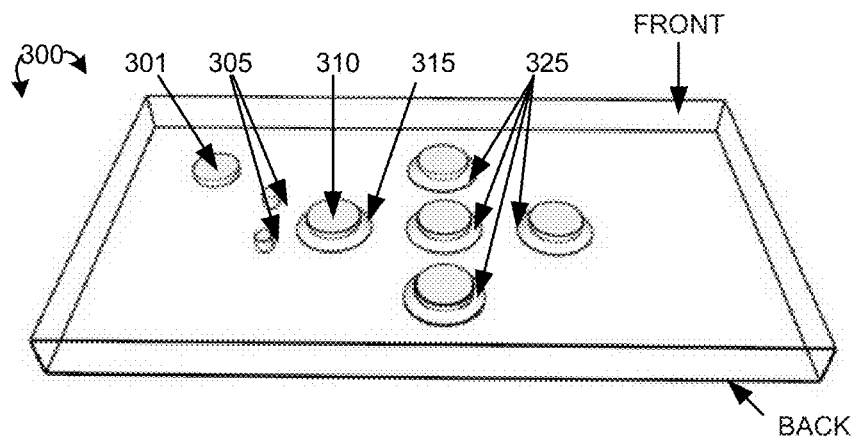
FIG. 3 shows an exemplary installation of the acoustic-to-electric sensors and LEDs on a waveform collecting and transmission module.

FIG. 3 shows an exemplary installation of the acoustic-to-electric sensors and LEDs on a waveform collecting and transmission module 300. In one exemplary configuration, one acoustic-to-electric (ATE) sensor 301 is installed at the front of the waveform collecting and transmission module. The front side is the side of module 300 that does not touch the body of the user. ATE sensor 301 detects the environment background. A micro-acoustic chamber 315 is used to enhance the body acoustic signals. Micro-acoustic chamber 315 is mounted on the back of waveform collecting and transmission module 300. An acoustic-to-electric sensor 310 is mounted on top of a micro-acoustic chamber 315. In one exemplary installation, four other micro-acoustic chambers and acoustic-to-electric sensors 325 are mounted on the back of the waveform collecting and transmission module 300. The number of acoustic-to-electric sensors in the device is determined by the sensitivity of sensor, the application environment, and the target price of the device. Having multiple acoustic-to-electric sensors enhances the signal strength. These sensors can be installed in a sunflower shape, with one in the center and the rest are around the center. The number of sensors and its arrangement can vary to fit different requirements. The considerations and/or criteria for the number of sensors includes cost consideration, and the environment of the intended use. For example, for a low cost device, whose usage is focused on quiet environment, single acoustic-to-electric sensor mounted on the back of the device without acoustic chamber can be used. Two LEDs 305 with different wavelengths are mounted at the front of the waveform collecting and transmission module 300. The different absorbing rate of the two wavelengths can determine the blood oxygen level of the user. LEDs 305 are used in conjunction with smart device camera or photodiode to form a simple pulse oximetry to measure the blood oxygen level. LEDs 305 with visible wavelength are also used as a status indicator.

Figure 4:
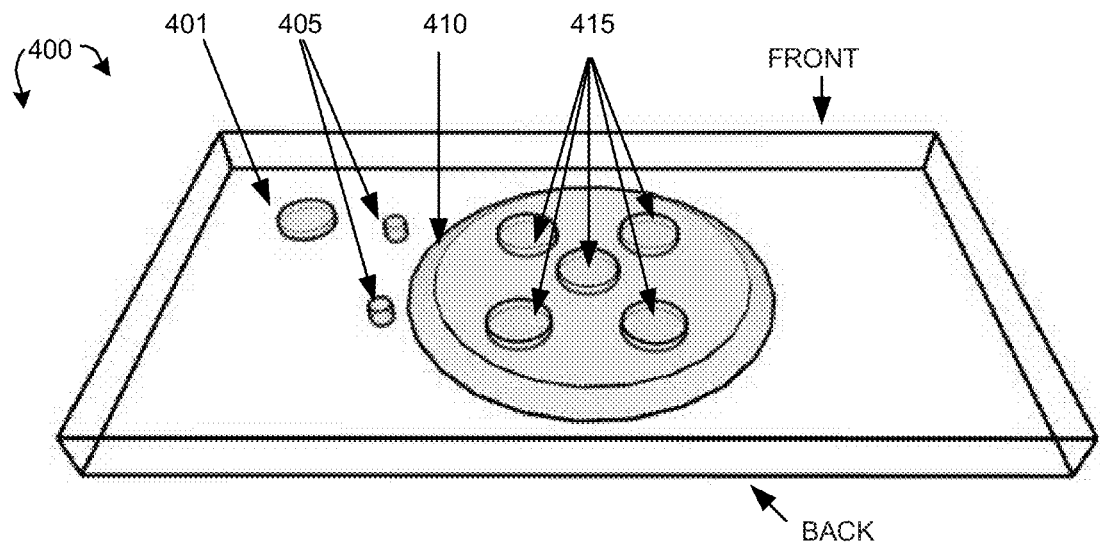
FIG. 4 shows an exemplary installation of the acoustic-to-electric sensors and LEDs on the waveform collecting and transmission module.

FIG. 4 shows an exemplary installation of the acoustic-to-electric sensors and LEDs on the waveform collecting and transmission module 400. In this installation, one acoustic-to-electric sensor 401 is installed at the front of the waveform collecting and transmission module. It is used to detect the environment background. A large acoustic chamber 410 is used to enhance the body acoustic signals. It is mounted on the back of the waveform collecting and transmission module 400. Multiple acoustic-to-electric sensors 415 are mounted on top of large acoustic chamber 410. In this installation, five acoustic-to-electric sensors 415 are mounted on the back of the waveform collecting and transmission module 400. Two LEDs 405 with different wavelengths are mounted at the front of the waveform collecting and transmission module. LEDs 405 are used in conjunction with smart device camera or photodiode to measure blood oxygen level. LEDs 405 with visible wavelength can also be used as a status indicator.

The waveform collecting and transmission module can be mounted on the user's body for more than 48 hours or longer. Unlike traditional clinical measurements that only collect for a few minutes, the wearable heartbeat device collects measurements for a much longer period. Therefore, it requires the module to be small and light-weighted. For example, in one embodiment the module weighs no more than couple of ounces, and having a diameter around one inch and as thin as possible. To reduce the height of the device, instead of using the traditional PCB, thin and flexible PCB is used. Another important issue needs to be resolved is how to mount the device on human body for a long time without discomfort. In one embodiment, the silicone gel patch, such as "ScarAway", can be used to help to mount the device. For mature female user, a special bra can be used to mount the device. An elastic belt can be used to mount the device during exercises. Since the waveform collecting and transmission module is very thin and lightweight, it can be put in a wallet or attached on the protection case of the smart phone or other smart device.

Figure 5:
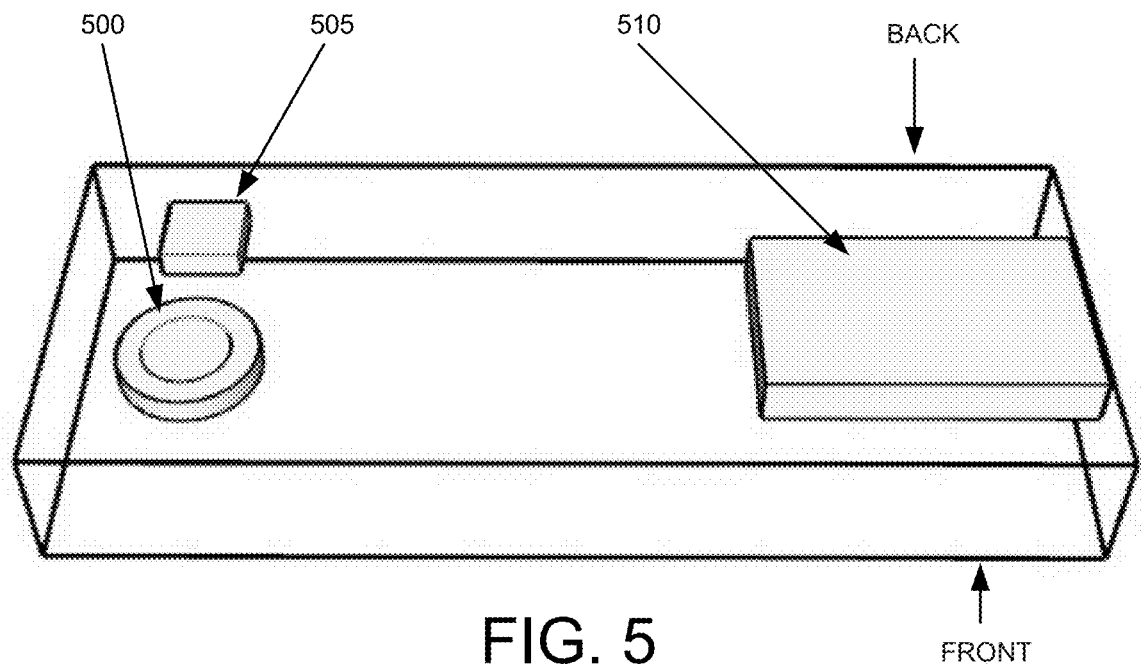
FIG. 5 illustrates a a waveform collecting and transmission module directly mounted on a special designed smart phone.

FIG. 5 illustrates a a waveform collecting and transmission module directly mounted on a special designed smart phone. 500 is the smart phone camera, 505 is the flashlight of the smart phone. A waveform collecting and transmission module 510 is mounted at the bottom of the smart phone. The module is automatically charged using the smart phone battery when it is mounted on the smart phone.

Figure 6:
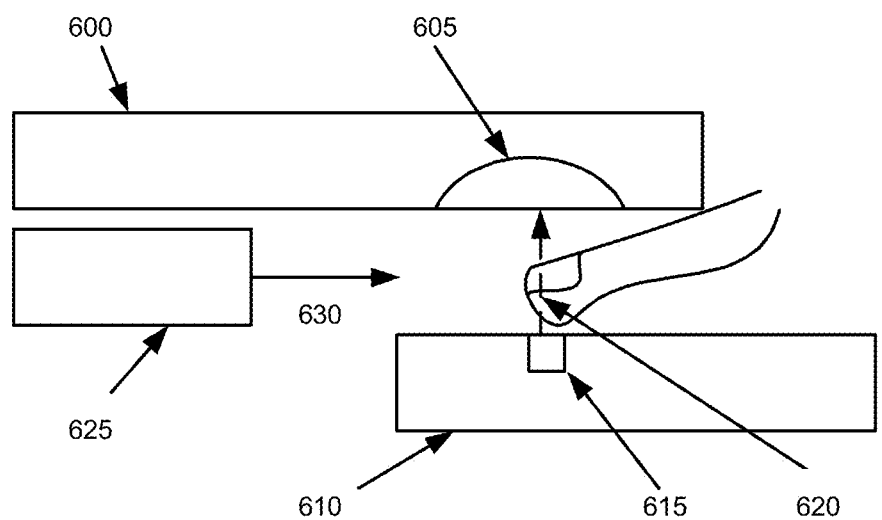
FIG. 6 is an exemplary diagram of measuring the blood oxygen level using a smart device 600 and a waveform collecting and transmission module.

FIG. 6 is an exemplary diagram of measuring the blood oxygen level using a smart device 600 and a waveform collecting and transmission module. Smart device 600 has a camera or photodiode 605. The waveform collecting and transmission module has LEDs 615. In one sample usage, a user puts his/her finger between smart device's camera 605 and LEDs 615 of the waveform collecting and transmission module 610. Smart device 600 can send command through local wireless network, such as Bluetooth, to waveform collecting and transmission module 610 to turn on one LED with one wavelength then turn on the other LED 620 with different wavelength. Smart device 600 uses its camera to capture two images from the two LEDs in waveform collecting and transmission module 610, respectively. Smart device 600 takes a first image with a first LED on in module 610. Smart device 600 then takes a second image with a second LED on in module 610. Smart device 600 can also use its photodiode to detect the light strength of the two LEDs from waveform collecting and transmission module 610. By comparing these two images or the signals strength that detected by the photodiode, smart device 600 can get the blood oxygen level of the user based on predefined algorithm. In order to get the accurate measurement, a calibration process is needed. A neutral media, such as transparent glass or plastic block with the thickness closed to human finger 625 is inserted 630 between the smart device and LEDs; Smart device 600 takes the measurements with LEDs 615 turned on. Smart device 600 collects such measurements as a baseline for the calibration. It is understood by one of ordinary skills in the art that other calibration methods can also be used.

In one embodiment, a executable program can be installed on the smart device, the computer or the dedicated embedded system to control the waveform collecting and transmission module. The executable program can also display waveform in real time. The executable programs can also retrieve the stored waveform for display. The waveform can be stored in the non-volatile storage of the smart device or the heartbeat collecting and transmission module. The executable program can store and transmit the stored waveform from the waveform collecting and transmission module to the remote data center. This process can be fully automatic or can be manually controlled by the user. It can also receive and display analysis reports, historic waveform archives, and reports on a remote data center. In some embodiments, the executable program accepts user inputs and relays questions, algorithms requests and acceptable financial awards of the services to the remote data center or third party medical professionals, data analysis and data mining expertise.

In accordance to embodiments of the current invention, privacy management is enabled. A user can use the smart device, the computer or a dedicated embedded system to manage privacy. The smart device or other devices receives user inputs, determine whether to release his/her personal information based on predefined algorithm. The smart device or other devices so configured may also determine whether to release waveform, analysis reports to medical professional as diagnosis reference. Similarly the smart device or other devices may determine if releasing his/her personal information, waveform, analysis reports to third party for analysis, research, and data mining usage.

Figure 7:
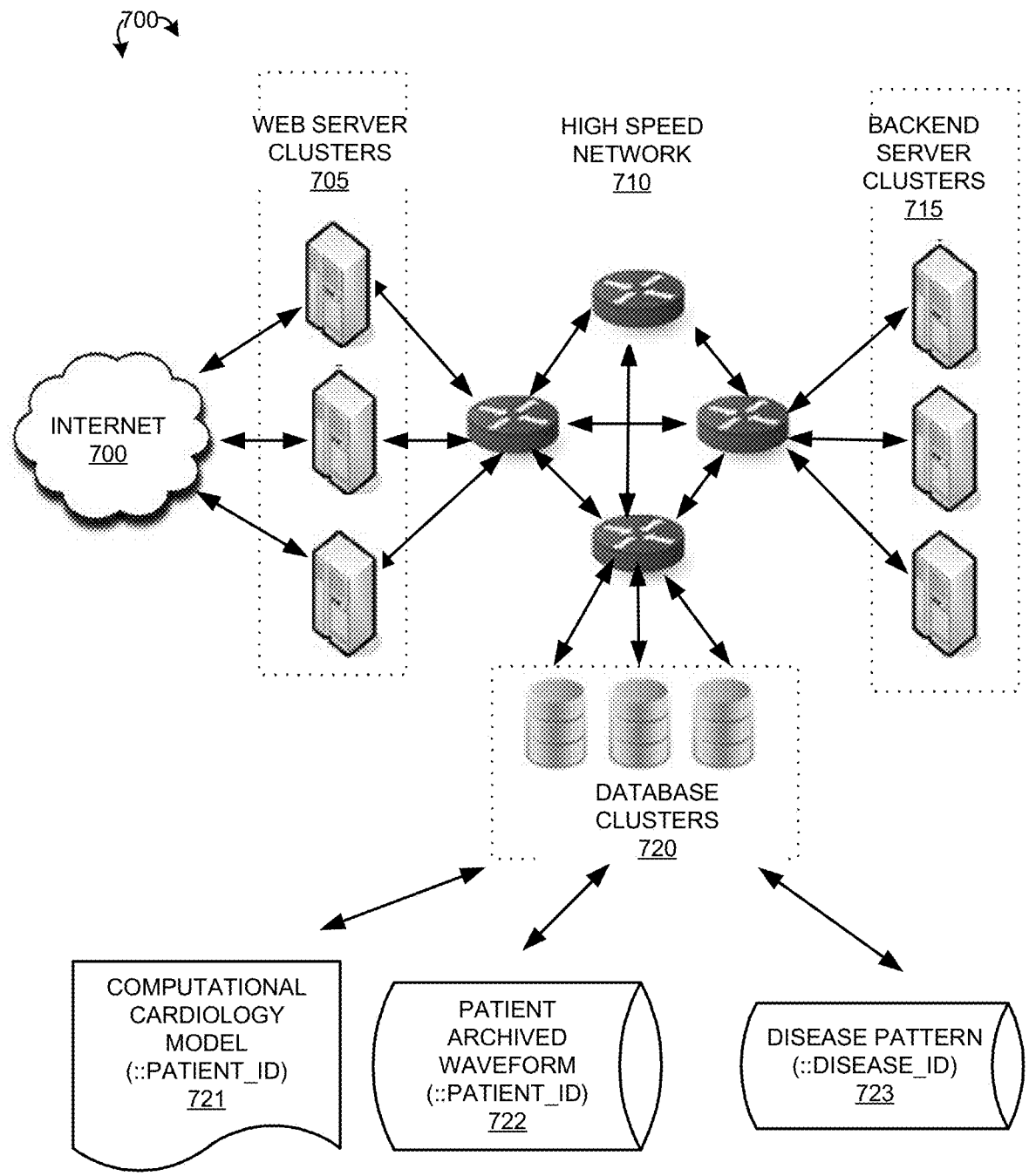
FIG. 7 illustrates a network 700 with a remote data center in accordance with embodiments of the current invention.

FIG. 7 illustrates a network 700 with a remote data center in accordance with embodiments of the current invention. Network 700 consists of web server clusters 705, database clusters 720, and back end server clusters 715. These clusters are interconnected by a high-speed network 710. Smart device 105, computer 110 or local server 115 can connect to web server clusters 705 through an Internet 701 and transmit the waveforms data into the database clusters 720 of the remote data center. Back end server clusters 715 will get the waveforms from database clusters 720. Database clusters 720 stores achieved waveform information of patients, processes the information, and stores the process results including report into database clusters 720. Database clusters 720 may have multiple specific databases, such as computational cardiology mode database 721, patient archived waveform database 722, and disease pattern database 723. The user can use the smart device 105, computer 110 or local sever 115 to view the analysis results, manage the account and archives, subscribe third party analysis algorithms. The web server clusters 705 take the roles as mediators to monitor the active user number, distribute the storage workload and computational workload, and make sure load balancing between servers. FIG. 7 only demonstrates one data center, as the user base growth, multiple data centers will be employed.

Figure 8:
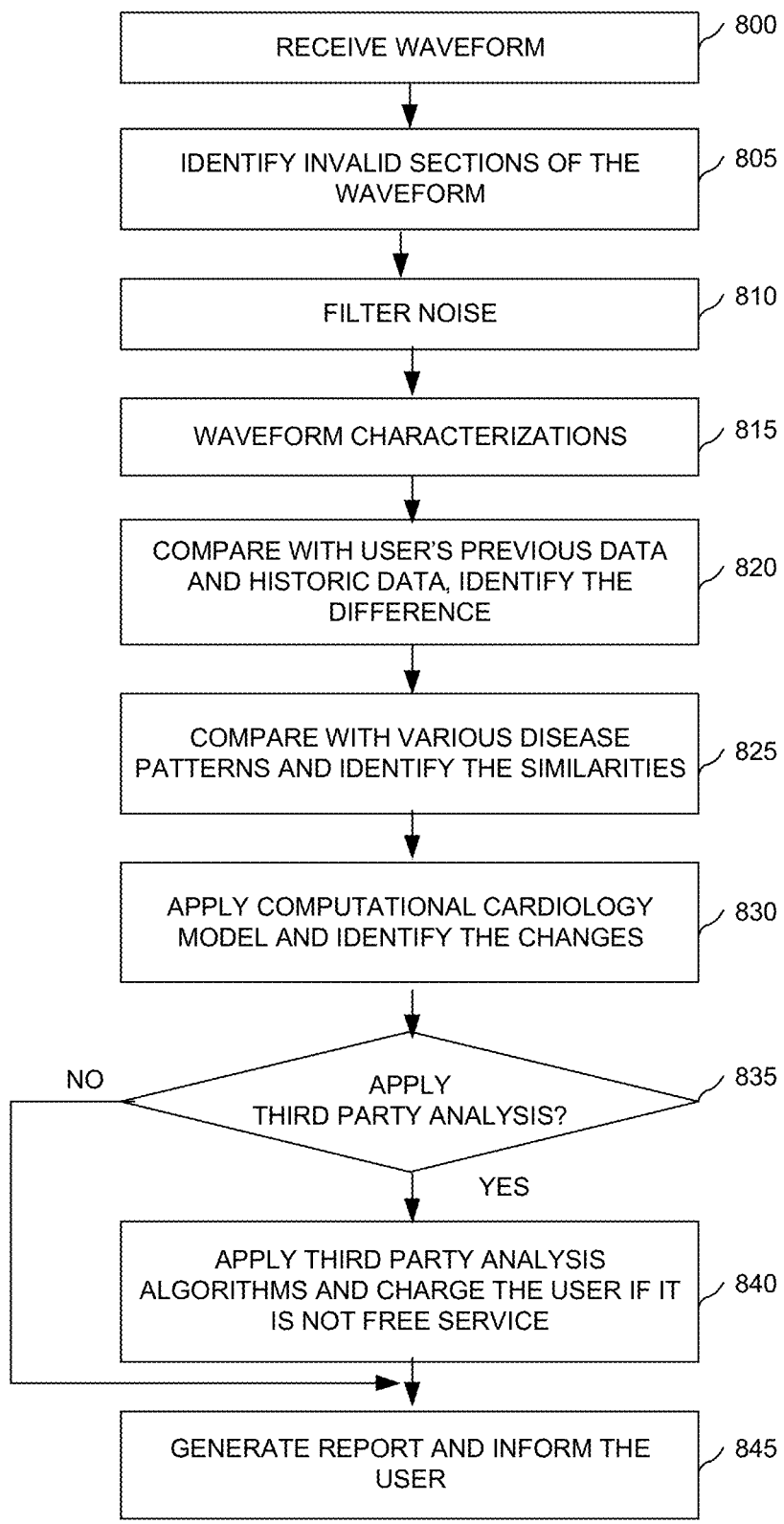
FIG. 8 shows a block diagram of waveform processing in accordance with embodiments of the current invention.

FIG. 8 shows a block diagram of waveform processing in accordance with embodiments of the current invention. The remote data center receives waveform 800 and stores them into a database such as database 720. Generally speaking, the body waveform is weak signal comparing to environment background, such as loud music, machine operation noise, etc. It is very likely that certain parts of received waveform contain overwhelming environmental background. In another scenario, certain parts of the received waveform may contain very weak signal or invalid signal due to improper mounting of the collecting device. The next stage of the process is to identify the invalid sections of the received waveform 805. The later processes will skip these sections. For the valid sections of the received waveform, noise filter 810 is employed to filter out body noise and environmental noise. At next stage, waveform characterization 815 is performed to extract characterization parameters. For the heartbeat waveform, the heartbeat rate is calculated, the heartbeat intervals are measured, irregular heartbeat intervals will be identified, and abnormal heartbeat waveform sections are also identified and marked for further analysis. These preliminary characterization results will be stored into the database.

The movement sensors waveform is used to determine the status of the body. For example, the server will know if the user is in a calm status, or is under active movement or exercises based on the movement sensors waveform. Based on the determined status of the body, the server can choose proper characterization algorithms, and proper data set to compare against in the later analysis phase. The characterization results will be used to compare with user's historic data 820. The differences are analyzed to see if the changes are toward health direction or unhealthy direction. The analysis results and conclusion will be stored into a database such as database 720. Further, the abnormal sections of the waveform are compared against various disease patterns to find matches or identify similarities 825. The analysis results will be stored into a database such as database 720.

Computational cardiology model of the user can be used to predict the waveform. The valid sections of received waveform will compare against predicted waveform. If there are mismatches, a end server, such as back end server 715, will adjust the parameters to try to match the received waveform. These adjustments are analyzed to conclude if they are toward healthy direction or unhealthy direction. If the back end server failed adjustments, failed reasons are reported. The matching details, adjustments, conclusions, failure reports can be stored into a database, such as database 720. The user can pre-select third party analysis algorithms 835. According to user's selections, the back end server will apply the pre-selected third party algorithms to the valid sections of the received waveform 840. The analysis results and reports can be stored into the database. If the third party's analysis algorithms are not free, the user will be charged for the service 840, and the charge detail will be recorded into the database. In the end, the back end server will summarize all the analysis results, reports from different stages and generate a general report 845. This report will be stored into the database. When the report is ready, user will be informed through a web server, such as web server 705 by email, SMS, or other methods. The user can also login the web server to view the report and analysis details.

Figure 9:
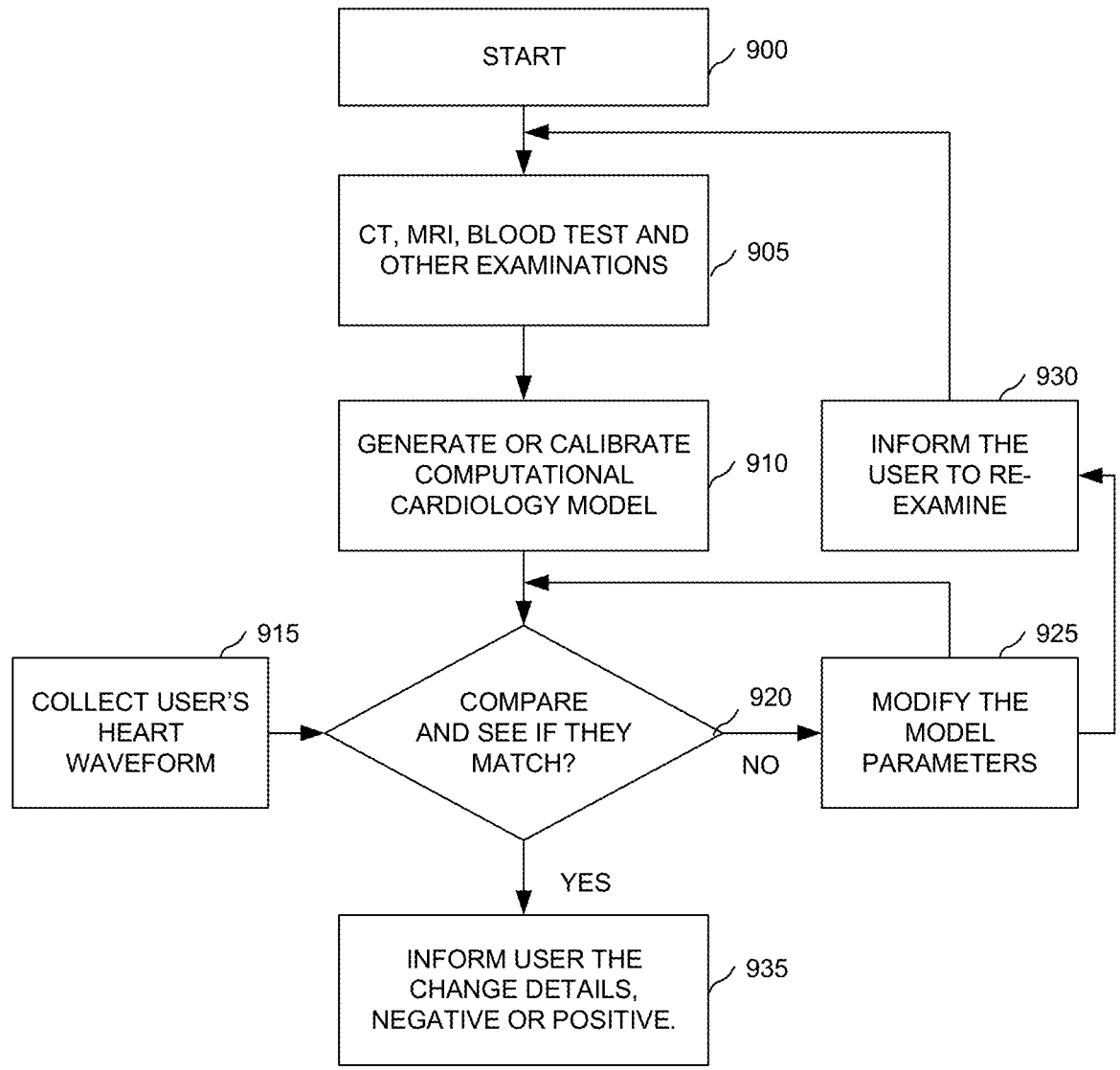
FIG. 9 shows a block diagram of generating a computational cardiology model for a user and predicting the user's heartbeat waveform based on the model.

FIG. 9 shows a block diagram of generating a computational cardiology model for a user and predicting the user's heartbeat waveform based on the model. Modern medical research has discovered that human heart functions more like a mechanic device which periodically pumps blood into blood vessels then relaxes. One proof is that human can survive many months by using an artificial heart which is a man-made mechanic device. In order to obtain the computational cardiology model, the user can take CT and MRI images at step 905 during heart pumping, relaxation and in-between phases. The detailed structures of user's heart and blood vessels can be obtained. The dynamic changes during heart pumping, relaxation and in-between movements can be used to determine the elastic resistance of the heart and blood vessels. Blood test and other medical examinations can help to determine the blood viscosity. Based on these parameters, a computational cardiology model can be built for the user at step 910. If the user already has a model, this process can be used to calibrate the previous model. At step 915, the user's heartbeat waveform is collected. Step 920 determines if the computed waveform of the user and the waveform collected from the user matches. If step 920 determines a mismatch, at step 925, the parameters of the model is adjusted based on the difference and the waveform is re-calculated until they match. However, after significant adjustments, if the calculated waveform still fails to match the collected waveform, this result is recorded into the database at step 930. Step 930 may additionally inform the user of the failure. If the calculated waveform does match the collected waveform, the adjustments is summarized at step 935. Step 935 also determines if the adjustments are toward health direction or unhealthy direction. All these are stored into the database. When the report is ready, user will be informed through the web server, such as web server 705 by email, SMS, or other methods. The user can also login the web server to view the report and analysis details.

In one embodiment of the present invention an open platform is used as a remote server. The open platform remote data server allows third party to utilize the collected waveform to do analysis and data mining. The algorithms developed by the third party can be utilized by the remote server. Meanwhile, charging model can be built so that the third part can be financially benefited from its contribution. The service provider, individual user, or user group can post specific requests for the third party. The charge can be per analysis charge, or one time charge to fulfill certain requests.

Figure 10:
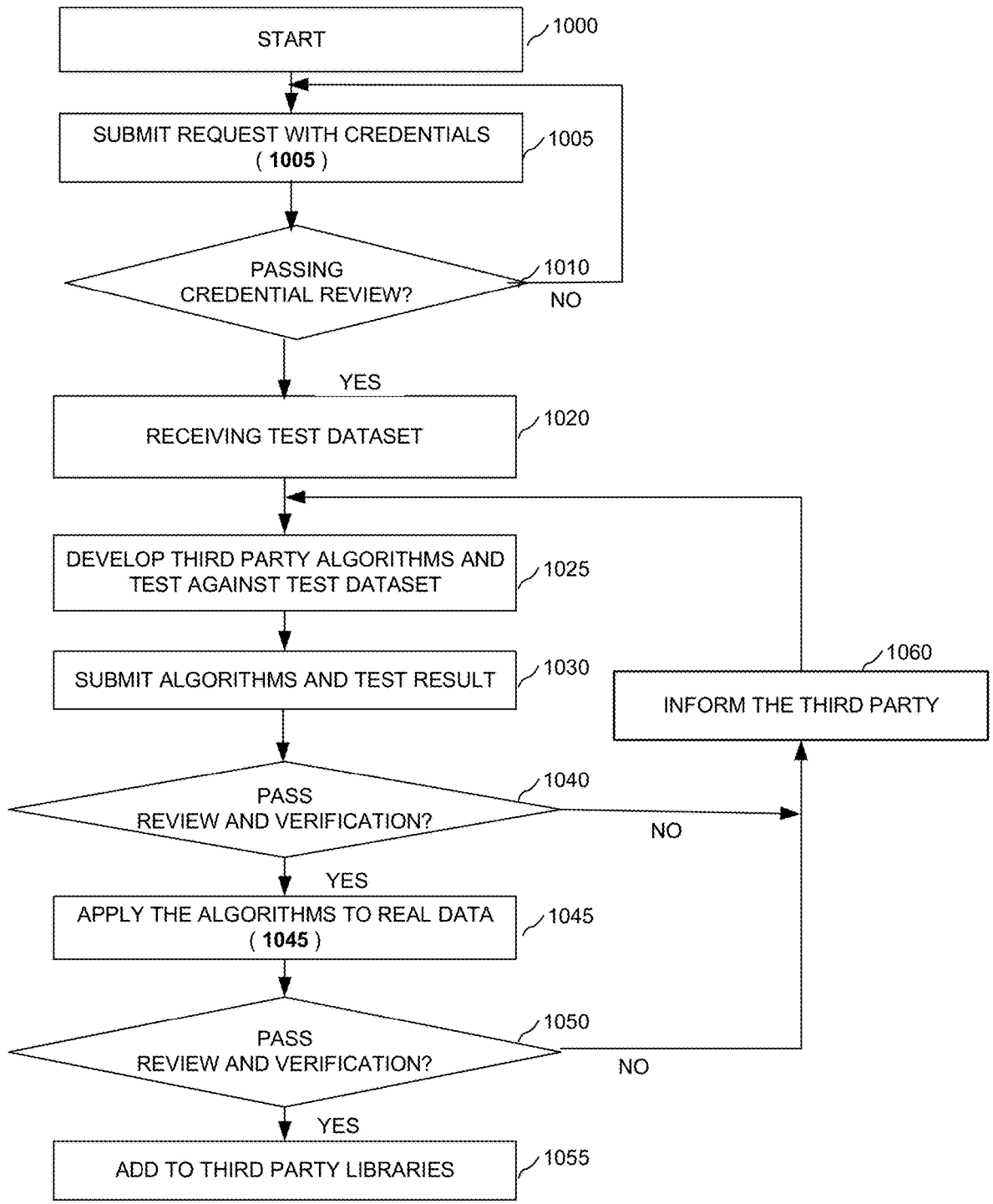
FIG. 10 shows a block diagram of the third party application and verification process in accordance with embodiments of the current invention.

FIG. 10 shows a block diagram of the third party application and verification process in accordance with embodiments of the current invention. The first step of the process is to submit the request with credentials 1005. The credentials include diploma, publications, patents and awards. A review committee will review the request and credentials at step 1010 and give recommendation. If the third party request is granted, the third party needs to sign a set of legal documents 1015, such as non-disclosure agreement, non-competitive agreement, charge agreement, etc. After legal process, the third party will receive test dataset 1020. The dataset can be from the service provider, individual user or user group. Based on the test dataset, the third party can start algorithm development and test the algorithm using the test dataset 1025. Then the third party can submit the algorithms and test result 1030. A committee including technical expertise, service provider, individual user or user group will review and verify the algorithms. If the algorithms fail during review and verification, the committee will inform the third party the failed reasons so that the third party can improve its work 1060. If the algorithms pass the review and verification, they will be applied to real service for waveform analysis, characterization, or data mining 1045. Further review and verification will be conducted 1050. If the third party algorithms pass, they will be added into third party libraries for user to choose 1055.

Figure 11:
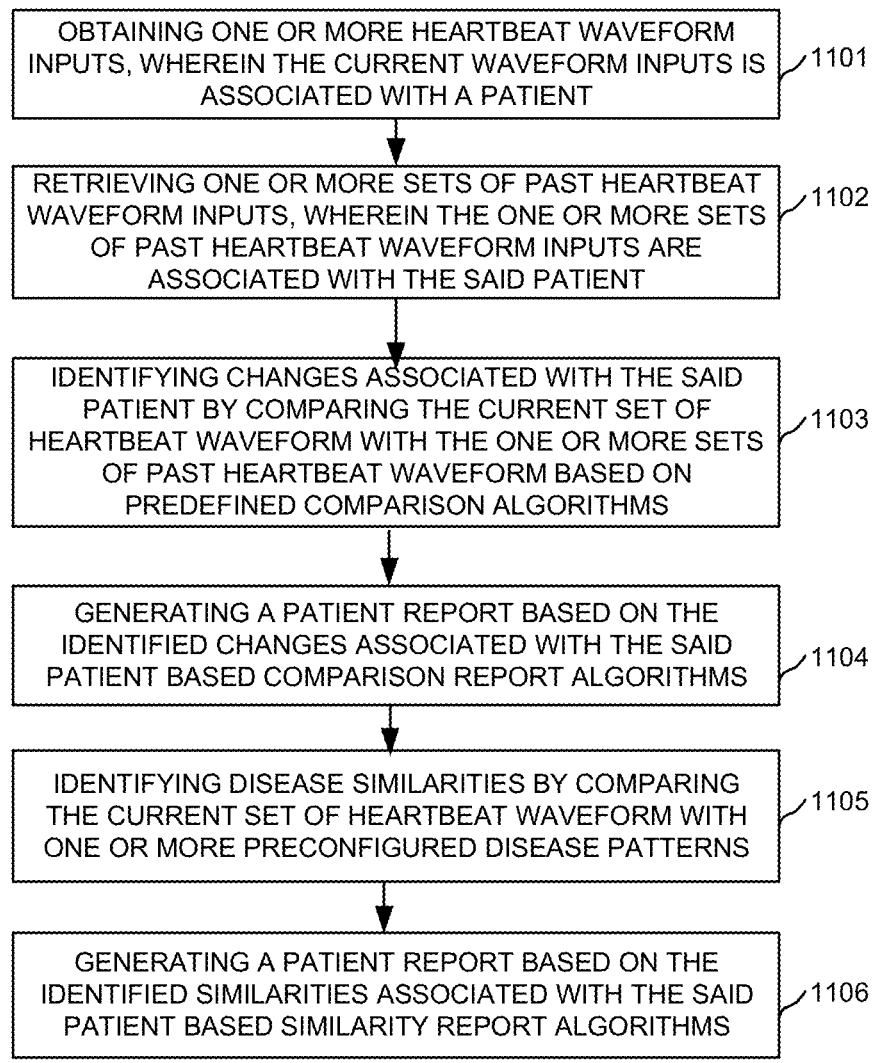
FIG. 11 is a flow chart analyzing received heartbeat waveform inputs based on past heartbeat waveform inputs and identifying changes in accordance with embodiments of the current invention.

FIG. 11 is a flow chart analyzing received heartbeat waveform inputs based on past heartbeat waveform inputs and identifying changes in accordance with embodiments of the current invention. Step 1101 obtains one or more heartbeat waveform inputs, wherein the current waveform inputs is associated with a patient. Step 1102 retrieves one or more sets of past heartbeat waveform inputs, wherein the one or more sets of past heartbeat waveform inputs are associated with the said patient. Step 1103 identifies changes associated with the said patient by comparing the current set of heartbeat waveform with the one or more sets of past heartbeat waveform based on predefined comparison algorithms. Step 1104 generates a patient report based on the identified changes associated with the said patient based comparison report algorithms. Step 1105 identifies disease similarities by comparing the current set of heartbeat waveform with one or more preconfigured disease patterns. Step 1106 generates a patient report based on the identified similarities associated with the said patient based similarity report algorithms.

Although the present invention has been described in connection with certain specific embodiments for instructional purposes, the present invention is not limited thereto. Accordingly, various modifications, adaptations, and combinations of various features of the described embodiments can be practiced without departing from the scope of the invention as set forth in the claims.

What is claimed is:

1. A method comprising:
    obtaining one or more current acoustic heartbeat waveform inputs continuously by a wearable local device, wherein the one or more current heartbeat waveform inputs is associated with a user, and wherein the wearable local device collects acoustic heartbeat waveform inputs through a series of acoustic sensors arranged within the wearable local device to receive sound from different directions;
    retrieving one or more past acoustic heartbeat waveform inputs, associated with the said user;
    identifying changes associated with the said user by comparing the current one or more acoustic heartbeat waveform inputs with the one or more past acoustic heartbeat waveform inputs of the user based on predefined comparison algorithms; and
    generating a user report based on the identified changes associated with the said user based comparison report algorithms, wherein the user report comprises at least one of report elements comprising: one or more similarities with one or more preconfigured disease patterns, and a direction of the input as being towards healthier or towards unhealthier.

2. The method of claim 1 further comprises:
    identifying disease similarities by comparing the current one or more heartbeat waveform inputs with one or more preconfigured disease patterns; and
    generating a user report based on the identified similarities associated with the said user based similarity report algorithms.

3. The method of claim 1, wherein the current one or more heartbeat waveform inputs is obtained from a remote wearable device via a network connection.

4. The method of claim 1, wherein the current one or more heartbeat waveform inputs is obtained from a smart device via a network connection, and wherein the smart device obtains an original heartbeat waveform from a wearable device.

5. The method of claim 1, wherein the comparison algorithm involves applying an algorithm developed by a certified third party by the local device.

6. The method of claim 1, wherein the one or more past heartbeat waveform inputs is retrieved from a cloud-based database.

7. The method of claim 1, wherein the comparison algorithm involves:
    retrieving or generating a computational cardiology model of the said user, wherein the computational cardiology model predicts a heartbeat waveform;
    identifying differences between the current heartbeat waveform and predicted heartbeat waveform through the computational cardiology model;
    adjusting parameters of the computational cardiology model to match the current heartbeat waveform; and
    generating a comparison report based on the adjusted parameters.

8. The method of claim 1, further comprising:
    identifying one or more invalid signal sections of the current one or more heartbeat waveform inputs based one a predefined validation algorithm wherein valid signal sections are identified by skipping the one or more invalid signal sections.

9. The method of claim 8, further comprising:
    applying filter to the valid signal sections to filter out body noise and environmental noise.

10. The method of claim 1, further comprising:
    characterizing the current one or more heartbeat waveform inputs based on a predefined characterization algorithm, wherein the characterizing extracts characterization parameters.

11. The method of claim 10, wherein the characterizing involves at least one of characterization comprising: calculating a heartbeat rate, measuring heartbeat intervals, identifying irregular heartbeat intervals, and marking one or more identified irregular heartbeat intervals.

12. The method of claim 1, further comprising:
    obtaining one or more movement waveform inputs, wherein each of the one or more movement waveform inputs associates with a corresponding current heartbeat waveform inputs, and wherein each movement waveform inputs indicates a movement status of the user.

13. The method of claim 12, wherein the movement status associated with the corresponding current heartbeat waveform is used in selecting a characterization algorithm, wherein the characterization algorithm applies to at least one of heartbeat characterizations comprising: calculating a heartbeat rate, measuring heartbeat intervals, identifying irregular heartbeat intervals, and marking one or more identified irregular heartbeat intervals.

14. The method of claim 12, wherein the movement status associated with the corresponding current heartbeat waveform is used in selecting a proper past heartbeat waveform inputs to compare with the corresponding current heartbeat waveform.

* * * * *